United States Patent [19]

Nösberger, Paul

[11] Patent Number: 4,700,009
[45] Date of Patent: Oct. 13, 1987

[54] PROCESS FOR PREPARING A SUBSTITUTED BENZALDEHYDE

[75] Inventor: Nösberger, Paul, Birsfelden, Switzerland

[73] Assignee: Hoffmann-La Roche Inc., Nutley, N.J.

[21] Appl. No.: 823,213

[22] Filed: Jan. 28, 1986

Related U.S. Application Data

[63] Continuation of Ser. No. 485,547, Apr. 15, 1983, abandoned.

[30] Foreign Application Priority Data

Feb. 28, 1982 [CH] Switzerland .............................. 2597
Feb. 24, 1983 [CH] Switzerland .............................. 1029

[51] Int. Cl.⁴ .............................................. C07C 45/36
[52] U.S. Cl. ..................................... 568/431; 568/432
[58] Field of Search ................................. 568/431, 432

[56] References Cited

U.S. PATENT DOCUMENTS 1,636,854 7/1927 Craver .................................. 568/431
3,423,466 1/1969 Guyer et al. ......................... 568/431

FOREIGN PATENT DOCUMENTS 0009239 4/1980 European Pat. No. ............. 568/431

*Primary Examiner*—Werren B. Lone
*Attorney, Agent, or Firm*—Jon S. Saxe; Bernard S. Leon; Richard J. Mazza

[57] ABSTRACT

The present disclosure is concerned with a novel process for the manufacture of substituted benzaldehydes, namely of benzaldehydes of the formula

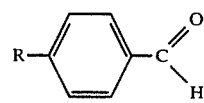

wherein R represents a methoxy or tert.butyl group.

The compounds of formula I are known substances, useful as, e.g. intermediates.

12 Claims, No Drawings

PROCESS FOR PREPARING A SUBSTITUTED BENZALDEHYDE

This is a continuation of application Ser. No. 485,547 filed Apr. 15, 1983 abandoned.

BACKGROUND OF THE INVENTION

European Pat. No. 9239 describes the steam phase catalytic oxidation of compounds of the formula:

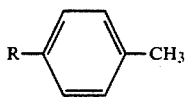

wherein R is methyl, methoxy and t-butyl to produce the corresponding aldehydes using a complex molybedenum catalyst of the formula $Mo_{12}Me_a{}^1Me_b{}^2Me_c{}^3Me_d{}^4O_x$ where $Me^1$ is one or more of the elements Bi, Co, Ni, Fe, W, Nb, Ta; $Me^2$ is one or more of the elements K, Rb, Cs, Tl, In; $Me^3$ is one or more of the elements P, B, Sb, V, Sr, Cr; $Me^4$ is one or more of the elements Mn, Re, Pd, Ir, Rh, Cu, Sn; Zn, Sm, Mg, Ce, Ag, Li, As, Ba, Ca; a=0-24 (if W≠0→0,5-110); b=0.01-0.2 (if Bi, V or P>0,5→0,1-6); c=0-6 (if a=o→0,5-5); d=0-10 and x is the number of oxygen atoms needed to satisfy the valencies of the other elements.

DESCRIPTION OF THE INVENTION

The process provided by the present invention comprises oxidizing a compound of the formula

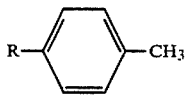
II wherein R has the above significance, in the presence of oxygen or oxygen-containing gases and a metal oxide catalyst of the composition $$MoMe_a{}^1Me_b{}^2O_x \qquad \text{III}$$

wherein $Me^1$ stands for copper or silver and $Me^2$ stands for one or more of the elements Ti, Zr, Fe, Co, Ni, Zn, Sn, Pb, Sb, Bi, B, P or a rare earth metal, a denotes 0.2 to 1.0, b denotes 0 to 0.5 and x denotes the number of oxygen atoms required to satisfy the valencies of the other elements present at temperatures of 350° to 600° C.

The process is characterized by high selectivity (amount of compound I in the reaction product, namely

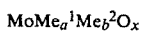

as well as by high converstion (ratio of reacted starting material II/starting material II used is high).

$Me^1$ preferably represents copper. $Me^2$ preferably represents iron, cerium, zinc or zirconium and particularly tin. The term "rare earth metal" is intended to denote the metals having the atomic numbers 21, 39 and 57-71.

The molar ratio of Mo to the sum of the remaining metals is preferably 1-3, especially 1.05-1.4.

The molar ratio of $Me^1$ to $Me^2$ is preferably greater than about 2; it especially amounts to 5-30.

In order to achieve especially pronounced activities of the catalyst it has been found to be convenient, especially when b=0 or when b has small values, to add talc or silicon dioxide having a large specific surface (e.g. >100 m²/g).

The catalyst can be present in pure form, can be mixed with an inert carrier material or can be fixed on an inert, shaped carrier material (preferably in the form of balls). Examples of inert carrier materials are α-aluminium oxide, ceramics, kieselguhr, diatomaceous eath, glass, silicon carbide, calcinated silicon dioxide and the like. Catalysts which are fixed on an inert carrier material are preferably used. α-Aluminium oxide and ceramics are preferred carrier materials.

The process in accordance with the invention can be carried out in a fluidized bed or preferably in a packed bed reactor.

Oxygen or, preferably, an oxygen-containing gas is used as the oxidizing agent in accordance with the invention. The term "oxygen-containing gas" signifies herein in general a mixture of oxygen and an inert gas such as, for example, nitrogen, carbon dioxide, argon and steam. The oxygen content in the educt stream is not critical. However, it generally amounts to about 1-40 vol.% and preferably to about 5-15 vol.%. It is especially preferred to use air to which can be added, if desired, nitrogen and/or exhaust gases from the reactor (after separation of the aldehyde) in order to modify the course of the reaction and to remove reaction heat.

The amount of oxygen or oxygen-containing gas is not critical. In order to achieve a sufficient conversion, at least about 1 mol of oxygen should be added to the reactor per mol of educt II. However, the reaction is advantageously carried out with an excess of oxygen, for example with about 200-2000% and preferably with about 300-1000% excess.

The content of the toluene II in the starting mixture can vary within a wide range, although naturally the spontaneous ignition temperature and the explosion limits of II must be taken into consideration. However, the educt concentration should generally amount to about 0.5-10 vol.%, preferably 1-3 vol.%.

The contact times should generally lie in the range of 0.1 to 10 seconds, the range of about 0.1 to 0.5 seconds being preferred.

The pressure at which the reaction is carried out is not especially critical. The reaction is advantageously carried out at atmospheric pressure, but it can also be carried out at higher or lower pressures.

The oxidation of the educt II in accordance with the invention is strongly exothermic and temperature dependent. The optimum temperature is dependent on the catalyst used, the oxygen and educt concentration in the educt stream, the gas velocity, the form and size of the reactor and the like. The oxidation is generally carried out in a temperature range of about 350° to about 600° C., preferably about 400° to about 500° C. A temperature range of about 430° to about 470° C. is especially preferred.

As reactor materials there can be used basically all conventional materials which in practice do not affect the educt and product under the reaction conditions, examples of such materials being stainless steel, glass, ceramics and the like.

The amount of catalyst is not critical. The amount used is especially dependent on the temperature, the form and size of the reactor and the amount of educt used. The optimization is conveniently carried out by charging the catalyst and, if desired, inert carrier material into the reactor (preferably a packed bed reactor) and then adjusting the residence time and the temperature so that the conversion of educt is optimal. Where the catalyst is introduced on to a shaped carrier (e.g. ceramic balls), then the amount of catalyst amounts to about 2–10%, perferably 4–8%, of the amount of carrier used.

In order to obtain the product I, the product stream is cooled and the condensible constituents are separated in this manner. As mentioned above, a portion of the exhaust gases can be added to the reactor again as a diluent. The condensed organic products are separated in the usual manner (e.g. distillatively) and the unreacted starting material together with the low-boiling by-products are recycled.

The catalysts can be prepared readily in a manner known per se; for example, by combining an aqueous solution of $Me^1/Me^2$ salts (preferably the nitrates) with an aqueous solution of ammonium heptamolybdate/ammonia, filtering, washing with water, optionally fixing on a carrier and calcinating (e.g. at 450°–600° C.). However, the filtration and the washing can be omitted. In this case, the calcination is preferably carried out in the reactor and in an adequate gas stream (e.g. air). In this case, the temperature is increased initially to 200° C. and thereafter slowly (corresponding to the evolution of nitrous gases) to the desired calcination temperature. The calcination provides that the metals are usually present in the highest oxidation state.

In formula III x is accordingly also the number of oxygen atoms which result formally from the number of existing metal, boron and phosphorus atoms and their highest oxidation states.

The following Examples illustrate the present invention:

EXMPLE 1

The reactor consists of an electrically heated evaporation tube (400° C., length 20 cm) and a reaction tube (length 60 cm, diameter 3.5 cm), which is surrounded by an air bath having circulation and which is connected at the upper end with the evaporation tube. The tube portions are constructed from stainless steel. The evaporation tube as well as the upper and lower parts of the reaction tube are filled with ceramic balls, the middle 34 cm of the reaction tube are filled with catalyst. The catalyst was prepared as follows:

600 g of ceramic balls having a diameter of 4–5 mm were coated with a suspension of 0.25 g of talc in 20 ml of distilled water in an 1.5 l coating pan. On the pretreated carrier there was coated 21.0 g of ammonium heptamolybdate tetrahydrate, 24.6 g of copper II nitrate trihydrate, 1.6 g of zinc II chloride and 3.7 g of cerium III nitrate hexahydrate in 550 ml of distilled water. The speed rotation of the pan, the air stream (400° C.) and the addition of the metal salt solution were adjusted so that a temperature of 60°–70° C. was maintained in the carrier.

330 ml of this catalyst were introduced into the reactor and heated to 200° C. with an air stream of 220 l/h until the formation of nitrous gases subsided. Subsequently, the temperature was increased gradually to 500° C. and the catalyst was calcinated at this temperature for 3 hours; formal composition of the catalyst: $MoCu_{0.86}Zn_{0.10}Ce_{0.07}O_x$.

The air bath temperature was reduced to 390° C. and 24 ml of p-tert.butyl-toluene and 220 l of air were added hourly to the evaporator. Analysis of the reaction products gave a conversion of 58% and a selectivity relative to p-tert.buty-benzaledhyde of 35%. The yield of the aldehyde $$\left(\frac{\text{Aldehyde I formed}}{\text{II used}} \times 100 \left[\frac{\text{mol}}{\text{mol}}\right]\right)$$

amounted to 20%.

EXAMPLE 2

The procedure described in Example 1 was repeated, but the air supply was reduced to 120 l/h and 100 l/h of exhaust gases were recycled. 31% of the recycled p-tert.butyl-toluene reacted. The yield of aldehyde amounted to 13% and the selectivity was 43%.

EXAMPLE 3

A catalyst having the formal composition $MoCu_{0.45}Zr_{0.05}O_x$ was prepared as follows:

A solution of 19.8 g of copper II nitrate trihydrate and 3.9 g of zirconium IV nitrate pentahydrate in 35 ml of distilled water was added to a stirred solution of 32.1 g of ammonium heptamolybdate tetrahydrate and 8 g of ammonia (25%) in 150 ml of distilled water. The precipitate was filtered off under suction, washed with 60 ml of distilled water, suspended in 600 ml of distilled water and applied to 600 g of ceramic balls in a manner analogous to that described in Example 1. The catalyst was subsequently calcinated at 550° C. for 16 hours.

The testing of the catalytic activity was carried out in a manner analogous to that described in Example 1. 200 l of air and 24 ml of p-tert.butyl-toluene were added hourly to the reactor at an air bath temperature of 410° C. 58% of the p-tert.butyl-toluene reacted. The yield of aldehyde amounted to 22% and the selectivity was 38%.

EXAMPLE 4

The procedure described in Example 3 was repeated, but the air bath temperature was increased to 420° C. and the air supply was reduced to 100 l/h. In addition, 100 l/h of exhaust gases from the reactor were recycled. The conversion amounted to 50% and the yield and the selectivity relative to aldehyde amounted to 21% and 42%, respectively.

EXAMPLE 5

A catalyst having the formal composition of $MoCu_{0.45}Zn_{0.05}O_x$ was prepared by adding a solution of 14.5 g of copper II nitrate trihydrate and 0.9 g of zinc II chloride in 26 ml of distilled water to a stirred solution of 23.6 g of ammonium heptamolybdate tetrahydrate and 5.9 g of ammonia (25%) in 110 ml of distilled water. The precipitate was filtered off under suction, washed with about 40 ml of distilled water, suspended in 400 ml of distilled water, applied to 440 g of ceramic balls in a manner analogous to that described in Example 1 and subsequently calcinated at 550° C. for 16 hours.

The testing of the catalytic activity was carried out in a manner analogous to that described in Example 1. The air bath temperature was adjusted to 440° C. 50 l of air, 150 l of nitrogen and 24 ml of p.tert.butyl-toluene were added hourly to the reactor. 29% of the p-tert.butyl-toluene reacted. The selectivity relative to p-tert.butyl-benzaldehyde amounted to 49% and the yield amounted to 14%.

EXAMPLE 6

A catalyst having the formal composition $MoCu_{0.43}Fe_{0.036}Ce_{0.036}O_x$ was prepared by adding a solution of 18.8 g of copper II nitrate trihydrate, 2.6 g of iron III nitrate nonahydrate and 2.8 g of cerium III nitrate hexahydrate in 35 ml of distilled water to a stirred solution of 32.1 g of ammonium heptamolybdate tetrahydrate in 150 ml of distilled water. 8 g of ammonia (25%) were subsequently added, the precipitate was filtered off under suction, washed with about 60 ml of distilled water, suspended in 600 ml of distilled water, fixed to 600 g of ceramic balls in a manner analogous to that described in Example 1 and calcinated at 550° C. for 16 hours.

The testing of the catalytic activity was carried out in a manner analogous to that described in Example 1. 24 ml of p-tert.butyl-toluene were added hourly to the reactor at an air bath temperature of 415° C. and an air and nitrogen supply of in each case 100 l/h. 57% of the p-tert.butyl-toluene reacted. The selectivity relative to p-tert.butyl-benzaldehyde amounted to 39% and the yield amounted to 22%.

EXAMPLE 7

A catalyst having the formal composition $MoCu_{0.43}O_x$ was prepared by adding a solution of 29 g of copper II nitrate trihydrate in 40 ml of distilled water to a stirred solution of 49.4 g of ammonium heptamolybdate tetrahydrate and 10 g of ammonia (25%) in 190 ml of distilled water. The precipitate was filtered off under suction, washed with about 40 ml of distilled water, suspended in 600 ml of distilled water, applied to 600 g of ceramic balls in a manner analogous to that described in Example 1 and calcinated at 500° C. for 16 hours.

The testing of the catalytic activity was carried out in a manner analogous to that described in Example 1. The air bath temperature was adjusted to 430° C. 400 l of air and 36 ml of p-tert.butyl-toluene were added hourly to the reactor. 31% of the p-tert.butyl-toluene reacted. The selectivity relative to p-tert.butyl-benzaldehyde amounted to 52% and the yield was 16%.

EXAMPLE 8

A catalyst having the formal composition $MoCu_{0.9}O_x$ was prepared by adding a solution of 27.3 g of copper II nitrate trihydrate in 50 ml of distilled water to a stirred solution of 22.24 g of ammonium heptamolybdate tetrahydrate in 350 ml of distilled water. The resulting suspension was applied to 600 g of ceramic balls in a manner analogous to that described in Example 1. The catalyst was introduced into a tube (diameter 5 cm) and held at 200° C. in an air stream of 200 l/h until the formation of fog in the exhaust gas subsided (about 1 hour). The temperature was subsequently increased gradually to 400° C. Prior to use the catalyst was calcinated at 550° C. for 16 hours.

The catalytic activity was determined as follows:

An electrically heatable vertical tube of stainless steel (diameter 2.4 cm, length 60 cm) was filled in the middle with 50 ml of catalyst and at the two ends with ceramic balls (diameter 6 mm). The catalyst was heated to 420° C. and 100 l of air and 12 ml of p-tert.butyl-toluene were added hourly to the reactor. The heating of the tube was adjusted so that the maximum temperature in the reaction zone amounted to 450° C. Analysis of the reaction products gave a conversion of 13.2%, a selectivity relative to p-tert.butyl-benzaldehyde of 66.9% and a yield of 8.8%.

EXAMPLE 9

The catalyst was prepared and tested in a manner analogous to that described in Example 8, but 6 g of talc were added to the ammonium heptamolybdate tetrahydrate solution. 25.8% of the p-tert.butyl-toluene used reacted. The selectivity relative to p-tert.butyl-benzaldehyde amounted to 55.1% and the yield amounted to 14.2%.

EXAMPLE 10

A catalyst having the formal composition $MoCu_{0.85}Sn_{0.05}O_x$ was prepared by adding a solution of 25.97 g of copper II nitrate trihydate in 50 ml of distilled water and a solution of 1.24 g of tin II chloride dihydrate in 20 ml of alcohol to a stirred solution of 22.24 g of ammonium heptamolybdate tetrahydrate in 300 ml of distilled water. For the rest, the preparation and testing were carried out in a manner analogous to that described in Example 8. 30.4% of the p-tert.butyl-toluene reacted. The selectivity relative to p-tert.butyl-benzaldehyde amounted to 59.5% and the yield amounted to 18.1%.

EXAMPLE 11

The testing was carried out in a manner analogous to that described in Example 10, but only 6 ml of p-tert.butyl-toluene were added hourly to the reactor. 51.2% of the p-tert.butyl-toluene reacted. The selectivity relative to p-tert.butyl-benzaldehyde amounted to 48.3% and the yield amounted to 24.7%.

EXAMPLE 12

The catalyst was prepared and tested according to Example 10; the maximum of the temperature in the reaction zone was 490° C. only. 42.4% of the initial p-tert.butyl-toluene were converted. The selectivity relative to the starting material was 68%, the yield was 28.8%.

I claim:

1. A process for preparing a benzaldehyde of the formula

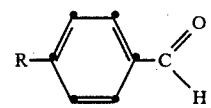

I wherein R represents a methoxy or tert.butyl group, which process comprises oxidizing a compound of the formula

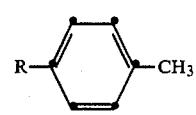

II wherein R is defined as above, in the presence of oxygen or oxygen-containing gases and a uranium-free metal oxide catalyst consisting essentially of the composition $$MoMe_a^1Me_b^2O_x$$

wherein $Me^1$ stands for copper or silver and $Me^2$ stands for one or more of the elements iron, cerium, zinc, tin, and zirconium, a denotes 0.2 to 1.0, b denotes 0 to 0.5 and x denotes the number of oxygen atoms required to satisfy the valencies of the other elements present, at temperatures of 350° to 600° C.

2. A process according to claim 1, wherein the catalyst additionally contains talc or silicon dioxide having a large specific surface.

3. A process according to claim 1, wherein $Me^1$ stands for copper.

4. A process according to claim 1, wherein $Me^2$ stands for tin.

5. A process according to claim 1, wherein R represents tert.butyl.

6. A process according to claim 1, wherein the reaction is carried out at a temperature of about 400° C. to about 500° C.

7. A process according to claim 1, wherein the reaction is carried out at a temperature of about 430° C. to about 470° C.

8. A process according to claim 1, wherein the reaction is carried out at atmospheric pressure.

9. A process according to claim 1, wherein there is used a catalyst which is fixed on an inert carrier material.

10. A process according to claim 1, wherein the contact time amounts to approximately 0.1 to approximately 10 seconds.

11. A process according to claim 1, wherein the reaction is carried out in an atmosphere comprising air to which optionally there may be added one or more of nitrogen and exhaust gases from the reactor.

12. A process for preparing a benzaldehyde of the formula

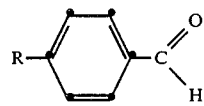

I wherein R represents a methoxy or tert.butyl group, which process comprises oxidizing at temperatures of 350° to 600° C. a compound of the formula

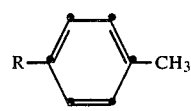

II wherein R is defined as above, in the presence of oxygen or oxygen-containing gases and a metal oxide catalyst of the composition $$MoMe_a^1Me_b^2O_x$$

wherein $Me^1$ stands for copper and $Me^2$ stands for tin, a denotes 0.2 to 1.0, b denotes 0 to 0.5 and x denotes the number of oxygen atoms required to satisfy the valencies of the other elements present.

* * * * *

UNITED STATES PATENT AND TRADEMARK OFFICE
CERTIFICATE OF CORRECTION

PATENT NO. : 4,700,009
DATED : October 13, 1987
INVENTOR(S) : Paul Nosberger

It is certified that error appears in the above—identified patent and that said Letters Patent is hereby corrected as shown below:

In the Title Page, under Foreign Application Priority Data, [30], the filing date for Swiss application No. 2597 should read April 28, 1982.

Signed and Sealed this

Fifth Day of April, 1988

Attest:

DONALD J. QUIGG

Attesting Officer

Commissioner of Patents and Trademarks